United States Patent [19]

Brown et al.

[11] 4,306,878

[45] Dec. 22, 1981

[54] METHOD OF SELECTING FLAME RETARDANTS FOR POLYMERS

[76] Inventors: Charles E. Brown, 3172 Glacier Dr., Hubertus, Wis. 53033; Charles A. Wilkie, 16240 Smith Dr., Brookfield, Wis. 53005

[21] Appl. No.: 182,422

[22] Filed: Aug. 29, 1980

[51] Int. Cl.$^3$ ............................................. G01N 24/08
[52] U.S. Cl. .............................. 23/230 PC; 23/230.3; 324/321; 422/78
[58] Field of Search ........... 23/230.3, 230 PC, 230 M; 422/78, 80, 68; 169/44, 45; 324/321, 300; 356/315

[56] References Cited

U.S. PATENT DOCUMENTS

| | | | |
|---|---|---|---|
| 3,789,060 | 1/1974 | Goering et al. | 23/230 M X |
| 3,868,221 | 2/1975 | Howard et al. | 23/230 PC X |
| 3,950,135 | 4/1976 | Whitesides | 23/230 M X |
| 3,953,171 | 4/1976 | Espitalie et al. | 23/230 PC X |
| 4,090,847 | 5/1978 | Becker et al. | 422/68 X |
| 4,120,660 | 10/1978 | Trizisky | 422/68 X |
| 4,254,373 | 3/1981 | Lippmad et al. | 324/321 |

FOREIGN PATENT DOCUMENTS 49-125096  11/1974  Japan ............................. 23/230 PC

OTHER PUBLICATIONS

ASTM D2863-70; May 8, 1970; "Standard Method of Test for Flammability of Plastics Using the Oxygen Index Method"; pp. 719-722.

Rev. Sci. Instrum., vol. 48, No. 10 (Oct. 1977); "NMR Probe for Combined Homonuclear Multiple Pulse Decoupling & Magic Angle Spinning"; Pembleton et al.; pp. 1286-1289; American Institute of Physics.

Journal of Applied Physics; vol. 22, No. 6 (6/1951); Nuclear Magnetic Resonance Study of Transitions in Polymers; Holroyd et al.; pp. 696-705.

*Primary Examiner*—Kenneth M. Schor
*Attorney, Agent, or Firm*—Quarles & Brady

[57] ABSTRACT

A method for selecting a flame retardant for a polymer comprises using cross polarization and magic-angle sample spinning techniques to record well resolved $^{31}$P and $^{13}$C nuclear magnetic resonance spectra of the polymer before and after ignition; recording $^{31}$P and $^{13}$C NMR spectra of the combination of polymer and a known flame retardant before and after ignition; characterizing the chemical and physical changes that occur in the flame retardant and the polymer upon ignition and thereby determining the chemical basis by which the known flame retardant is operating and using that knowledge to select another flame retardant that will be effective for use with the polymer.

2 Claims, No Drawings

METHOD OF SELECTING FLAME RETARDANTS FOR POLYMERS

The present invention relates to flame retardants for polymers. More particularly, it relates to a method of selecting effective flame retardants for polymers.

BACKGROUND OF THE INVENTION

The burning of a polymeric material may be considered as involving three steps as follows:

(1) The polymer is thermally degraded to smaller fragments.

(2) These fragments are volatilized and provide fuel for the flame.

(3) Energy is fed back to the surface of the polymer and thereby continues the formation of fuel by promoting thermal degradation of the surface and volatilization of the fragments. It is possible to retard the combustion process at any or all of these steps, and flame retardants are known that function in each of these ways.

The base polymer may itself be very resistant to thermal degradation or an additive that lessens the possibility of thermal degradation may be used. Polymers that contain a high aromatic content are known to be more resistant to thermal degradation than their aliphatic counterparts. For example, DuPont's Nomex, which is an aramid (highly aromatic polyamide) fiber made from m-phenylenediamine and isophtholyl chloride, is quite resistant. It also should be mentioned that wool is quite resistant. The polyphosphazenes are exceptionally resistant to thermal degradation. The phosphazene monomers may be used by themselves or copolymerized with another monomer to produce a polymer with the desired physical properties and thermal stability. For instance, a thermally stable polymer produced by the copolymerization of styrene and a phosphazene has been made.

An additive also might be utilized which will combine with the thermal degradation products in the condensed phase or the gas phase and render them either less volatile or less combustible. This is the main mechanism of action of the most common flame retardants.

Phosphorus containing flame retardants may function both in the condensed or in the vapor phase (as the halogens do). Elemental phosphorus has been used as a retardant for poly(ethylene terephthalate), but here the effect is mostly in the condensed phase. Both a change in the pyrolysis kinetics and an increased amount of char are observed. Red phosphorus is an effective flame retardant for oxygen containing substrates while it is only marginally useful for materials which do not contain oxygen. Triphenylphosphine oxide (Ph$_3$P-O), which functions exclusively in the vapor phase, also has been used as an additive for flame retardation of poly(ethylene terephthalate).

Inhibition of the energy feedback step of the combustion process may occur by increased formation of char, which functions as a thermal barrier and inhibits heat transfer. As noted above, red phosphorus in poly(ethylene terephthalate) functions partially in this way. The synergistic combination of ammonium poly-phosphate and cyanoethylated phosphine, which is an effective flame retardant system for polypropylene, owes at least part of its effectiveness as a flame retardant to the increased char formation.

Another means to reduce the thermal feedback is by producing gases by decomposition of the retardant that will cool the flame. Many of the inorganic retardants function to some extent by this process. Typical inorganic retardants are ammonium salts of carbonates, phosphates, or sulfates that cool the flame by production of NH$_3$, CO$_2$, SO$_2$, etc.

The use of hydrated alumina as a flame retardant typifies the fact that a retardant does not function in only one way but rather shows some effect in many of the burning steps. Alumina trihydrate (Al$_2$O$_3$.3H$_2$O) competes with the substrate polymer for absorption of heat when the sample is brought into contact with an ignition source and thus slows the rate at which the temperature of the substrate polymer rises. At about 220 degrees C. the alumina trihydrate molecule decomposes via a very endothermic dehydration reaction. The evolved water vapor then reduces the decomposition of substrate by diluting and cooling the flame from combustion of the gaseous products.

The thermal decomposition of polyolefin type materials (e.g. polyethylene, polypropylene, etc.) proceeds by a random scission mechanism commencing at 290° C. Since an additive must be stable at the processing temperature of 250° but must undergo decomposition or reaction with the substrate at ca 300°, phosphorus retardants are limited to the more thermally stable oxides, acids, and phosphonium salts. Flame retardancy may be achieved by the synergistic combination of ammonium polyphosphate with either phosphine oxides, phosphonium salts and similar materials. It is known that ammonium polyphosphate alone functions in the condensed phase, presumably by combining with the degradation products and rendering them less volatile or less combustible. No char formation is observed. The phosphonium salts or oxides alone function primarily in the gas phase and presumably as radical traps. Again no char formation is observed. However, the synergistic combination is active in the condensed phase, and a large amount of char is produced. Presumably these combinations are effective by thermally shielding the polymer from the flame. Another class of phosphorus retardants which is useful for polyolefin formulations is shown below.

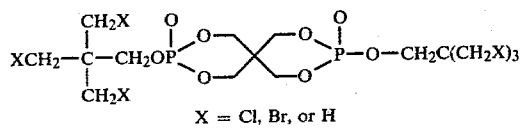

X = Cl, Br, or H

The primary decomposition pathway of poly(ethylene terphthalate) [PET] and presumably other oxygen containing polymers (polyesters, urethanes, etc.) is by a random scission of an ester linkage. Retardants that have been utilized include triphenylphosphine oxide (Ph$_3$PO), tris(2,3-dibromopropyl)phosphate(BrCH$_2$CHBrCH$_2$O)$_3$PO, (commonly referred to as Tris), polymeric phosphonate and elemental (red) phosphorus.

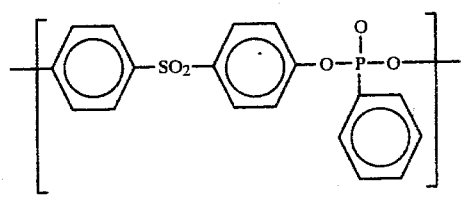

The first two additives are assumed to function primarily in the gas phase as radical traps. The mode of action of the above compound has not been disclosed but presumably both it and red phosphorus function in the condensed phase. As noted above red phosphorus is believed to inhibit secondary reactions, which lead to the volatile products that feed the flame, and to give rise to an increased char formation. It appears that some additives, notably red phosphorus, are quite effective for polymers containing oxygen while other classes (e.g. cyanoethyl phosphines) are effective for polymers with an all carbon backbone.

Two pathways are known for the decomposition of cellulose; these are dehydration and depolymerization. The main product of the dehydration process is a carbonaceous char along with small amounts of oxidizable materials (notably carbon monoxide), whereas the depolymerization pathway produces little or no char and all oxidizable materials. Clearly then an additive that promotes the dehydration pathway at the expense of the depolymerization pathway will be expected to provide less fuel to the flame and thus function as a flame retardant.

The treatment of cellulose with the adduct $PCl_3.2DMF(DMF=(CH_3)_2NC(O)H)$ results in the loss of DMF and chloride ion and the incorporation of phosphorus into the cellulose. The mode of action is probably associated with forcing the dehydration reaction since an increase in additive concentration (beyond a lower limit) increases the amount of char.

A synergistic effect is observed when an additive containing both phosphorus and nitrogen is utilized. Materials containing phosphorus linked directly to nitrogen are inherently more efficient than those not containing a direct link. The formation of phosphoramidates during pyrolysis has been suggested as a possible basis for the synergism. The ease of hydrolysis of the P-N bond and the relative inefficiency of the reaction have hampered further development of these materials.

The additives that appear to be most important for flame retardation in cellulose are the tetrakis (hydroxymethyl) phosphonium salts $((HOCH_2)_4P+$, (referred to as THP)). Unlike the $PCl_3.2DMF$ case, there is no chemical bonding between the cellulose and the additive at normal temperature. Instead THP is polymerized with urea, and this polymer then is physically mixed with the cellulose. It is believed that the additive is thermally degraded during combustion to phosphoric and polyphosphoric acids, which then function by catalyzing dehydration.

The additives that function as flame retardants are different for each of the classes of polymers. Thus, there are certain chemical and possibly physical requirements that must be fulfilled in order for flame retardation to occur. These requirements could involve bond-making between the retardant and the substrate (as is noted with cellulose and $PCl_3.2DMF$) or catalytic control of the reaction pathway during combustion.

The chemical changes that are involved in flame retardation may involve reaction of the retardant or a thermal degradation product of the retardant with the substrate or a thermal degradation product of the substrate. However, little is known of the basic chemistry that occurs on the surface of the burning polymer in the presence and absence of flame retardants for the simple reason that the chemical analysis of solids is difficult and requires chemical degradation of the sample.

SUMMARY OF THE INVENTION

It is the general object of the present invention to disclose a method for selecting effective flame retardants for polymers.

The method of the present invention for selecting effective flame retardants for a specific polymer comprises (a) measuring the chemical changes which occur in the polymer using cross polarization (CP) and "magic-angle" (MA) sample spinning techniques to record well resolved $^{31}P$ and $^{13}C$ NMR (Nuclear Magnetic Resonance) spectra of the polymer before and after ignition; (b) using the same techniques to record the NMR spectra of combinations of the polymer with flame retardants which are known to be effective which indicates the variations and changes in the polymer with the flame retardant present and changes in the flame retardant; (c) making a comparison of variations observed in (a) and (b); and (d) thereby determining the chemical basis by which the effective flame retardant is operating, and predicting, based on the knowledge of the chemical structure of the known effective flame retardants employed and the information measured and recorded, which other compounds will be effective as flame retardants for that specific polymer. In a preferred embodiment, samples of the combinations of known flame retardants and the polymer are subjected to stepwise controlled ignition with the CPMA $^{13}C$ NMR and CPMA $^{31}P$ NMR spectra recorded after each step. On the basis of the subtle chemical changes which take place on the polymer for flame to occur and the knowledge of the chemistry of the known effective flame retardant it is possible to predict which other compounds will be effective flame retardants for that polymer.

The changes in the chemical structure of the flame retardant, the substrate and the combination that are found with NMR spectrometry can be correlated with the results of the established oxygen index (OI) and UL94 procedures for the measurement of flame retardancy.

The inventive method thus provides previously unattainable data concerning the condensed-phase chemistry of polymer combustion and the chemical basis of flame retardation in polymers. For the first time, subtle chemical changes that occur on the polymer during combustion and flame retardation can be measured by NMR spectrometry with good resolution and them compared with quantitative measurements of retardancy. The results provide new insights into the basic chemistry of flame retardation and not only make it possible to predict which flame retardants will be effective with a given polymer, but also make it possible to design, synthesize and test more effective flame retardants.

DESCRIPTION OF THE PREFERRED EMBODIMENT

In the preferred embodiment of the present invention samples of all possible combinations of a polymer and either known or potential effective flame retardants, e.g., a phosphorous-containing compound, are made. The flame retardancy of each of the combinations and of the pure polymer substrate is quantitated using accepted flame retardancy procedures, and in parallel experiments the effect of "controlled ignitions" on the chemical structure of the combinations and of the pure polymer substrates is determined with $^{13}C$ and $^{31}P$ nuclear magnetic resonance measurements of the polymerized sample. The "controlled ignitions" consist of heating the samples to a fixed temperature for a fixed period of time (initially 10 minutes) and then cooling the samples to room temperature. The NMR spectra of the polymer is then taken to determine what chemical changes have taken place. The procedure is repeated cyclically with the same sample with the temperature raised an additional 50 degrees in each cycle. This is continued until the sample no longer is suitable for spectroscopy. In this way the chemical changes that occur at various temperatures are determined and can be correlated with the effectiveness of added phosphorus compound flame retardant. The "controlled ignitions" are conducted in different atmospheres, including $O_2$, $N_2$, $N_2O$, air and vacuum, to determine whether the effective flame retardants are functioning in the condensed phase. In this manner the chemical basis of the effective flame retardation by a known or putative flame retardant in the condensed phase can be ascertained. In addition, the results can be used to predict why a compound which is an effective flame retardant in one polymer is useless when combined with a different polymer.

The following test procedures are employed in the inventive method

Solid State NMR Spectroscopy

The frequency of resonance of a nucleus depends on the strength of the external magnetic field and on the environment of the nucleus. Each nucleus of a particular isotope within a molecule, such as $^{31}P$, will resonate at a slightly different frequency from the others depending on the functional group of which it is a part. This "shielding" of the nucleus from the external magnetic field that gives rise to these differences in resonance frequency is dependent upon not only the identity of the functional group but also on the orientation of the functional group and of neighboring functional groups and molecules. In the gaseous and liquid states these differences in environment are averaged by rapid tumbling so that only an average frequency of resonance is observed that is centered at the frequency of resonance characteristic of that functional group. In the solid state, rapid motion is not possible or is not isotropic or both. Therefore, an array of resonances is observed corresponding to all the orientations of the functional group and of its neighboring molecules. In addition to the frequency of resonance, the relaxation rate of the excited nucleus from the high energy to the low energy level also is dependent upon the orientation and distance of other nuclei. This dependence of relaxation rate is the result of dipolar coupling with the magnetic moments of these other nuclei, which produce small fluctuations in the observed external magnetic field. In the gaseous and liquid states these dipolar interactions are modulated by the rapid, isotropic rotational and translational motion of the molecules. In the solid state the interactions are not modulated by isotropic motion, and, since the dipolar fields are the result of a specific orientation of the dipoles with respect to the applied field, the dipolar broadening is much larger. In the solid state these two effects of chemical shift anisotropy and dipolar broadening produce line widths measured in kilohertz. By comparison, the line widths of resonances in liquids are on the order of 0.1 to 1 Hz. Thus, the primary concern of the NMR spectroscopist who wishes to study nuclei in solids is to preferentially reduce the chemical shift anisotropies of the dipolar broadening or both in such a manner as to resolve the very broad "powder pattern" to an understandable spectrum analogous to that of liquids. These techniques are well developed and equipment is commercially available for these experiments.

a. Enhancement of Resolution and Sensitivity

Two techniques have been developed to improve the resolution and increase the sensitivity of NMR spectra of solids. The first is called "magic-angle spinning", and is used to reduce the line broadening from chemical shift anisotropy. The second technique is to use various pulse sequences to reduce dipolar broadening. These techniques can be used together to produce well resolved spectra or can be used separately to distinguish among the various mechanisms of line broadening.

Magic Angle Sample Spinning

It can be demonstrated that many parts of the Hamiltonian for a solid spinning at the magic angle (54°44' from the magnetic field) are identical to those for the liquid phase. Thus, when a solid sample is spun at this angle the orientation effects that cause variations in the chemical shift are averaged to much the same extent as they are from rapid tumbling in the liquid. The "liquid-like limit" is approximated when the solid sample is spun at a rotation frequency greater than the line width of the powder pattern. Since these lines are measured in kilohertz, the main technical requirements associated with this technique are to use a rotor that is capable of withstanding the required high rotation frequency of 1–10 KHz and to use a stator that is capable of keeping the axis of rotation of this spinning rotor as close to the magic angle as possible.

Multiple Pulse Techniques

The multiple-pulse experiment is analogous to spin decoupling in NMR of liquids but is performed at higher power. The cross polarization experiment establishes population distributions of $^1H$ and $^{31}P$ nuclei, which interact with each other and thereby change their respective Boltzman distributions. This maximizes the entropy of the system while maintaining the total energy constant. The experiment is performed by administering a pi/2 pulse to the protons along the Y axis in the rotating frame followed by a long pulse along the X axis in the rotating frame. During this long pulse to the protons, the $^{31}P$ nuclei are pulsed for a time to establish $^1H$-$^{31}P$ contact and then the free induction decay of the $^{31}P$ nuclei is recorded. These $^{31}P$ pulses are repeated as necessary to deplete the polarization of the protons while increasing the sensitivity to the $^{31}P$ nuclei. The time between pulses no longer has a connection to the relaxation time of the $^{31}P$ nuclei; instead it is determined by the relaxation time of the protons.

In the principle, observation of $^{31}P$ in the solid phase should require decoupling of every other nucleus in the sample, but in practice one need worry only about coupling of $^1H$ an possibly $^{31}P$ nuclei because the natural abundance of other nuclei with magnetic moments is small. It already has been demonstrated that dipolar broadening of $^{31}P$ nuclei in a single crystal by the more abundant $^1H$ nuclei can be almost totally eliminated simply by measuring a free induction decay in the presence of a decoupling field at the frequency of resonance of the protons. Cross polarization yields the same spectral results, but with a six-fold savings in time that resulted from being able to pulse more rapidly. The reason for this savings in time is that the $^{31}P$ nuclei must re-establish thermal equilibrium between pulses in the free induction decay experiment while the more rapidly relaxing $^1H$ nuclei must achieve thermal equilibrium in the cross polarization experiment. The reason for this difference is that, with cross polarization, the protons are pulsed with the decoupling field at a proper strength and frequency to cause the protons to "spin in unison" with the $^{31}P$ nuclei. The polarization of the abundant protons is transmitted to the $^{31}P$ nuclei very rapidly and results in an enhancement of the $^{31}P$ signal intensity with simultaneous narrowing of the peaks. Basically the same procedures are used to record CPMA NMR spectra of 13C nuclei in solids.

Combination of Magic Angle Spinning and Multiple Pulse Techniques

It should be kept in mind that the preceding discussion of Multiple Pulse Techniques has assumed that there were no chemical shift anisotropies, as could be approximated in a properly oriented single crystal. These techniques alone would not be expected to produce very narrow peaks in polycrystalline or amorphous solids. For these kinds of experiments it is necessary to reduce line broadening from chemical shift anisotropy with magic angle spinning and simultaneously to reduce heteronuclear and/or homonuclear dipolar coupling. It should be noted that cross polarization is an important tool for increasing the sensitivity when spectra of $^{13}C$ in solids are recorded, but may not be as important for detection of $^{31}P$ in solids. The natural abundance of $^{31}P$ is 100% and NMR is quite sensitive to this nucleus, spectra of $^{31}P$ in solids can be recorded with simple dipolar decoupling without the increased sensitivity that cross polarization can produce.

NMR Spectroscopy of Phosphorus

The utility of any spectral technique is related directly to the ease of obtaining spectra and to the ease of interpretation of spectra. The isotopic abundance of $^{31}P$ is 100%, and NMR is inherently quite sensitive to this nucleus. Therefore the sensitivity to "unenriched" phosphorus-containing samples is very good as compared for example to $^{13}C$ whose natural abundance is only 1.1%. In addition, the $^{31}P$ nucleus has a spin of $\frac{1}{2}$ and a chemical shift range of ca 700 ppm. This results in spectra with narrow, well resolved lines. Most phosphorus-containing compounds have only one or a small number of chemically different phosphorus nuclei, and their spectra are quite easy to resolve. The $^{13}C$ nucleus also has a spin of $\frac{1}{2}$ and a broad range of chemical shifts (ca 200 ppm), but the average sample often has $^{13}C$ nuclei in many different environments, which give rise to many closely spaced resonances. However, these resonances can be resolved in solids and provide direct information about chemical structure.

One of the most useful characteristics of the simple phosphorus spectra is the chemical (Table 1), which may be associated with a particular chemical structure. Thus changes that occur during a chemical reaction can be detected as a change in chemical shift. For example, conversion of OP(OMe)$_3$ to P(OMe)$_4$+ cause a change in chemical shift of 53 ppm (i.e. −2 ppm to 51 ppm). It has been demonstrated that the reaction products of (HOCH$_2$)$_4$P+ with urea all can be differentiated in solution. Although much less experience exists for $^{31}P$ in the solid state, the same useful information is to be had.

TABLE 1

| Chemical Shifts for Various Phosphorus Compounds[a] | | | |
|---|---|---|---|
| Compound | | Compound | |
| (CH$_3$O)$_3$P | 141 | Na$_3$PS$_4$ | 88 |
| (CH$_3$)$_3$PS | 60 | (CH$_3$O)$_4$P+ | 51 |

TABLE 1-continued

| Chemical Shifts for Various Phosphorus Compounds[a] | | | |
|---|---|---|---|
| Compound | | Compound | |
| (CH$_3$)$_3$PO | 36 | (CH$_3$)$_4$P+ | 25 |
| Na$_3$PO$_4$ | 6 | H$_3$PO$_3$ | 5 |
| H$_3$PO$_4$ | 0 | (CH$_3$)$_3$P | −62 |
| P$_4$ | −461 | | | a. in ppm relative to 85% phosphoric acid (OPA).

Experimental Techniques a. Preparation of Samples

The preparation of compounds for analysis requires techniques and equipment that are available in a reasonably maintained chemical laboratory.

b. Measurement of NMR Spectra

The measurement of well resolved NMR spectra of solid samples with cross polarization and "magic-angle" sample spinning techniques has reached a level of development that permits its direct application to this analysis. These spectra can be recorded, for example, on a Nicolet NT-150 NMR spectrometer with CPMA probes and supporting circuitry produced by the Nicolet Technology Corporation of Madison, Wis. The polymers can be used either as machined or molded cylinders that fit snugly into the rotor or as finely ground powders that are packed into the rotor. Fibers can be packed tightly into the rotors for measurement of their NMR spectra.

c. Demonstration of Flame Retardancy

Two techniques are used for demonstration of flame retardancy—the oxygen index (OI) procedure reported in NBS Symposium, Natl. Bur. Stand., (U.S.) Spec. Publ. No. 357, 1972, p. 159 and the standarized UL94 procedure from Underwriters Laboratories Inc., Subjects 94/746, Sept. 7, 1973.

The oxygen index procedure requires that a sample be burned in a vertically downward mode in an oxygen/nitrogen atmosphere of controlled composition. The oxygen concentration is reduced until the sample is extinguished. This limiting oxygen concentration is the oxygen index of the sample. This test is specific for a given material and shows very little effect on sample dimensions. Most organic materials have an oxygen index of less than 20 indicating that they will burn in air; the addition of a flame retardant raises the oxygen index to some higher value with the amount of increase indicating the degree of effectiveness of the retardant. The oxygen index method also provides a tool to elucidate the mode of action of a given retardant. Since the combustion chemistry of the flame should depend on the nature of the oxidant, a change to an oxidant other than O$_2$, for instance N$_2$O, should have a marked effect on a retardant that functions in the gas phase (i.e. the retardant should not be as effective). On the other hand, a retardant that functions in the condensed phase by affecting pyrolytic decomposition should not show a significant effect when the oxidant is changed.

A more stringent test is the UL94 procedure. The sample is held in a vertical position and ignited at the bottom for 10 seconds with a 1.6 cm-high Bunsen flame. After the flame extinguishes the sample is reignited. The sample is rated V-0 if the flame extinguishes within 5 seconds without dripping, V-1 if the flame extinguishes within 25 second without dripping and FB if longer times are required for flame to extinguish. A similar time scale would be used to compare putative flame retardants in various polymer substrates.

d. Comparison of NMR Data with Results of Flame Retardancy Test

The chemical changes that occur in a polymer and its flame retardant when the retardant does its job are measured. This requires that the polymer and the candidate flame retardant be tested spectroscopically both before and after a test ignition. The ability of the candidate flame retardant to retard the flame must be quantitated and then it must be determined whether there are characteristic chemical changes in either substrate or retardant that occur when a particular retardant is effective.

There is to date no unified theory to explain the activity of phosphorus retardants in chemical terms. The typical retardants (i.e, phosphonium salts or phosphine oxides, red phosphorus (white phosphorus is too reactive and black phosphorus presumably is not reactive enough), and inorganic phosphorus compounds) appear to have only their thermal stability in common. By running a methodical survey of the chemical changes that occur in various combinations of polymer substrates and candidate flame retardants during controlled ignitions, it is possible to determine which chemical changes are needed for effective flame retardation to occur. Once the basic solid-state chemistry of flame retardation is known, it is possible to develop on the basis of chemical reactivity, flame retardants with better effectiveness and fewer unwanted side effects.

The flame retardancy of each polymer-flame retardant combination and of the pure substrate polymer is quantitated with the tests of flame retardancy described above. In parallel experiments the effect of "controlled ignitions" on the chemical structure of the combinations and of the pure substrate polymers are determined with $^{13}C$ and $^{31}P$ NMR of the polymerized samples. The "controlled ignition" is to heat the sample to a fixed temperature for a fixed period of time (initially 10 minutes) and then to cool the sample to room temperature. NMR spectra of the polymer then are recorded to determine what chemical changes have taken place. This procedure is repeated cyclically with the same sample with the temperature raised an additional 50 degrees in each cycle. This is continued until the sample no longer is suitable for spectroscopy. In this way the chemical changes that occur at various temperatures can be determined and can be correlated with whether or not the added phosphorus compound is an effective flame retardant. The "controlled ignitions" can be conducted in different atmospheres, including $O_2$, $N_2$, $N_2O$, air and vacuum, to determine whether the effective flame retardants are functioning in the condensed phase. In this manner the chemical basis of effective flame retardation in the condensed phase might be ascertained. In addition, these experiments can provide insight into why an effective flame retardant in one polymer can be useless when combined with a different polymer.

The method of the present invention is broadly applicable and can be used with all known classes of polymers including vinylic polymers, condensation polymers and biopolymers. Representative polymers with which the method can be employed include polypropylene polystyrene, polysulfone, polyethylene terephthalate (PET) and cellulose.

We claim:

1. A method of determining the mechanism of action by which a known flame retardant is effective for a specific polymer so that the effectiveness of other compounds as flame retardants for that polymer can be predicted which method comprises:

(a) using cross polarization, and "magic-angle" sample spinning techniques to record well resolved $^{31}P$ and $^{13}C$ nuclear magnetic resonance (NMR) spectra for the combination of the polymer with the known effective flame retardant;

(b) submitting samples of the combination of the known effective flame retardant and the polymer to stepwise controlled ignition which consists of heating the samples to a fixed temperature for a fixed period of time and then cooling the samples to room temperature;

(c) measuring and recording the NMR spectra of the chemical components of the polymer and flame retardant combination before and after each step of the controlled ignition and;

(d) analyzing the chemical composition of the components of the polymer and the flame retardant combination which are present at each step to identify the mechanism by which the effective flame retardant is operating, thereby making it possible to predict which other compounds capable of functioning in a similar chemical manner will be effective as flame retardants for said polymer.

2. The method of claim 1 in which the controlled ignitions are conducted in different atmospheres selected from oxygen, nitrogen, nitrous oxide, air, and vacuum to characterize the differences in mechanisms of combustion.

* * * * *